(12) United States Patent
Tracy

(10) Patent No.: US 8,691,253 B1
(45) Date of Patent: Apr. 8, 2014

(54) SHARK REPELLENT

(76) Inventor: Rhonda Tracy, Glen Ellyn, IL (US)

( * ) Notice: Subject to any disclaimer, the term of this patent is extended or adjusted under 35 U.S.C. 154(b) by 790 days.

(21) Appl. No.: 12/467,455

(22) Filed: May 18, 2009

Related U.S. Application Data

(60) Provisional application No. 61/130,068, filed on May 28, 2008.

(51) Int. Cl.
| | |
|---|---|
| *A01N 25/00* | (2006.01) |
| *A01N 25/34* | (2006.01) |
| *A01N 25/08* | (2006.01) |
| *A01N 59/08* | (2006.01) |
| *A01N 59/02* | (2006.01) |
| *A01N 35/04* | (2006.01) |
| *A01N 35/02* | (2006.01) |
| *A01N 31/00* | (2006.01) |
| *A01N 27/00* | (2006.01) |
| *C10C 3/00* | (2006.01) |
| *B63C 9/00* | (2006.01) |

(52) U.S. Cl.
USPC ........... 424/405; 424/402; 424/408; 424/409; 424/661; 424/705; 208/22; 428/36.1; 441/80; 514/692; 514/694; 514/724; 514/762; 514/763; 514/764; 514/766; 514/918

(58) Field of Classification Search
USPC ................. 424/402, 405, 408, 409, 661, 705; 428/36.1; 208/22; 441/80; 514/692, 514/694, 724, 762, 763, 764, 766, 918
See application file for complete search history.

(56) References Cited

U.S. PATENT DOCUMENTS

| | | | | |
|---|---|---|---|---|
| 2,389,719 | A * | 11/1945 | Dinsley | 514/557 |
| 2,950,488 | A * | 8/1960 | Sabo | 441/116 |
| 3,051,235 | A * | 8/1962 | Banks | 166/261 |
| 3,077,288 | A * | 2/1963 | Henry | 222/5 |
| 4,490,360 | A * | 12/1984 | Antonik | 424/538 |
| 4,602,384 | A * | 7/1986 | Schneider | 441/103 |
| 4,917,280 | A * | 4/1990 | Schneider | 224/223 |
| 4,933,187 | A * | 6/1990 | Schneider | 424/497 |
| 5,407,679 | A * | 4/1995 | Hayes | 424/402 |
| 7,004,806 | B1 * | 2/2006 | Schneider | 441/1 |
| 2006/0024344 | A1 * | 2/2006 | Matos et al. | 424/405 |

\* cited by examiner

*Primary Examiner* — John Pak
*Assistant Examiner* — Nathan W Schlientz

(57) ABSTRACT

The invention relates to a method of use, of a mixture of chemical compounds for a shark repellent, as well as methods of protection garments in using such material(s). Generally, there are not many shark repellents. This shark repellent contains a mixture of chemical compounds that are highly toxic and trenchant, which will deter the shark from injured or non-injured humans or animals, once the mixture is immersed in water.

27 Claims, 5 Drawing Sheets

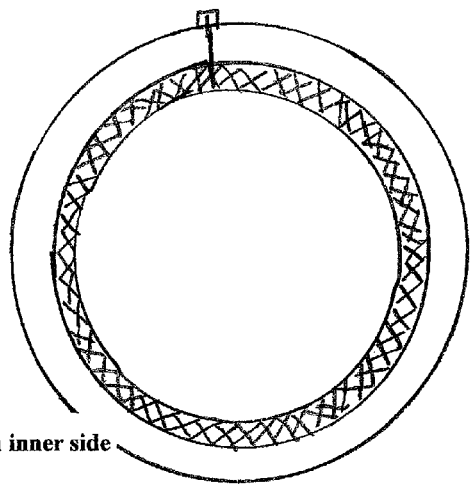
Figure 1. Belt with mesh on inner side
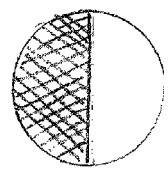
Figure 2. Cross section of belt and mesh
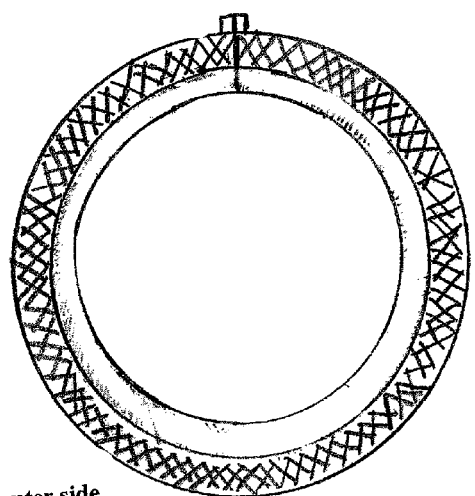
Figure 3. Belt with mesh on outer side Front section of vest with mesh Cross section of vest with mesh in front and back

Figure 6. Back section of vest

Wrist band anklet with mesh on outer side

Inner tube / floatation device with holes

Cross section of inner tube with holes

Cross section of inner tube with mesh

Inner tube / floatation device with mesh

Front section of garment with mesh

Cross section of garment with semi impervious or impervious layer with mesh.

Back section of garment with mesh

SHARK REPELLENT

RELATED APPLICATION

This application is the Non-provisional filing of Provisional application No. 61/130,068 filed May 28, 2008.

BACKGROUND OF THE INVENTION

The background of this invention covers chemical structures, toxicity, penetration (to enter or to go through) and partial solubility. The following articles further explains and underlines as to why such properties will be effective for this method of use in the shark repellent.

What is already known, as stated in Chromatography Online regarding compound identification, an article reads: "Crude oil is known as a very complex mixture of compounds with various elemental compositions and chemical structures. An important analytical task in the oil industry is to quickly identify compounds from crude oils that could potentially harm the production plant. Therefore, detailed and quantitative information about the compound types in crude oil is of high interest for a molecular-based management of the refining process." Sep. 2, 2007, Jens Fuchser, Matthias Witt.

"Sweet" crude oil has less sulfur than "sour" crude, whereas sour crude oil is the most common, and both having a "stink" or strong smell.

There are many published articles relating to crude oil being toxic. Petroleum is noted for its toxicity, as stated in a New York government web article: "Accidental releases of petroleum, toxic chemicals, gases, and other hazardous materials occur frequently throughout New York State. Even small releases have . . . ."
www.dec.ny.gov/chemical/8428.html—15k"

'The following article further relates to that of crude oil, and states that it penetrates the ground, contaminating soil, water and wildlife. It is a fossil fuel and a mixture of chemical compounds.

Herein, stated in web article, from http://corrosion-doctors.org/Pollution/oil-pipes.htm: "Oil Drilling in an Alaskan Wildlife Refuge Leaves a Toxic Legacy of Oil Spills and Pollution. Oil drilling in the Kenai National Wildlife Refuge in Alaska has resulted in hundreds of spills, fires and explosions and has contaminated massive amounts of soil and groundwater with oil and other toxic substances that are known to cause mutations and birth defects in wildlife. Scientists studying the area have uncovered frogs with crippling deformities . . . ."

The same article further states:
Spilled Oil and Other Contaminants Threaten Birds and Other Wildlife Crude oil and other toxic contaminants spilled by oil companies in Kenai National Wildlife Refuge threaten birds and wildlife with both lethal and sub-lethal effects.

Crude Oil: Exposure to crude oil causes kidney failure, liver failure, altered blood chemistry, reproductive impairment, lung damage, and nervous system damage in birds and wildlife. Crude oil destroys the insulating capacity of feathers and fur. In the brutally cold temperatures of Alaska, birds and wildlife that come into contact with spilled oil usually freeze and die.

Produced Water: Drawing oil and natural gas from the earth also extracts water from deep in the ground. Because this "produced" water has been in contact with petroleum sources and other minerals it contains hydrocarbons, salty brine and elevated concentrations of barium, beryllium, cadmium, chromium, copper, iron, lead, nickel, silver and zinc, and small amounts of natural radioactive metals. While the concentrations of some of these substances are small, the amounts of produced water released in spills can be enormous, posing a serious environmental threat.

Polychlorinated Biphenyls (PCBs): PCBs are thought to cause mutations, cancers, birth defects, endocrine disruptions, still births, nervous disorders, and liver disease. PCBs are ranked as one of the most hazardous compounds (worst 10%) to ecosystems and human health.

Benzene: A recognized carcinogen and developmental toxicant thought to cause mutations, cancers and birth defects. Benzene is ranked as one of the most hazardous compounds (worst 10%) to ecosystems and human health.

Xylene: Exposure to xylene can cause headaches, dizziness, lack of coordination, skin irritations, and breathing problems. Animal studies indicate that exposure to high xylene concentrations may cause delayed growth and development in unborn young."

Raw crude oil prior to refinement, is flammable, composed of compounds of hydrogen and carbon, and has a strong trenchant odor. Therefore, even raw crude oil is toxic as well as being flammable.

Partial Solubility:

Here in the following reference, it is explained that petroleum crude oil, has properties that are partially soluble in water:

Stanford, L. A.; Kim, S.; Klein, G. C.; Smith, D. F.; Rodgers, R. P. and Marshall, A. G., Identification of Water-Soluble Heavy Crude Oil Organics. Acidic and Basic NSO Compounds in Fresh Water and Sea Water by Electrospray Ionization Fourier Transform Ion Cyclotron Resonance Mass Spectrometry, *Environ. Sci. Technol.* 2007, 41, 2696-2702.

[a] Dept. of Chemistry and Biochemistry, Florida State Univ., Tallahassee, Fla. 32306, USA
[b] Korean Basic Science Institute, 52 Yeoeun-Dong, Yusung-Gu, Daejeon 305-333, Korea
[c] ICR Program, National High Magnetic Field Lab, Tallahassee, Fla. 32310-4005, USA "The first step in understanding petroleum crude oil spills is to identify which chemical components dissolve in water.

Here, we use ultrahigh-resolution magnet-based mass spectrometry to resolve and identify, for the first time, thousands of different chemical components of crude oil and water exposed to that oil. Of the 7,000+ acidic species identified in South American crude oil, surprisingly many are water-soluble, and many more in pure water than in seawater (see Figure. Top: crude oil. Bottom: water-soluble components). Water solubility depends on molecular weight, size, and heteroatom (nitrogen, oxygen, sulfur) content."

PRIOR ART

[Keeping in mind the prior patent of Schneider, U.S. Pat. No. 4,933,187—this shark repellent is not in totality derived from sodium sulfate material.]

With reference to Schneiders invention, and according to a Material Data Safety Sheet, Mallinckrodt Chemicals, J. T. Baker, Sodium Sulfate is described as follows, whereas it states in paragraph #3, that it is: "mildly toxic by ingestion." Moving down to paragraph #12, it further states that it's "not toxic to aquatic life."

Therefore, in consideration of these findings, this prior art does not relate to the present application of shark repellent.

REFERENCES

1. Product Identification
   Synonyms: Sodium sulfate decahydrate; disodium sulfate decahydrate; glauber's salt; sulfuric acid, sodium salt, decahydrate; sodium sulfate, 10-hydrate
   CAS No.: 7757-82-6 (Anhydrous) 7727-73-3 (Decahydrate)
   Molecular Weight: 322.20
   Chemical Formula $Na_2SO_4.10H_2O$
   Product Codes:
   J. T. Baker: 3890
   Mallinckrodt: 8012, 8027
3. Potential Health Effects
Inhalation:
Not expected to be a health hazard.
Ingestion:
Mildly toxic by ingestion. Systemic toxicity is unlikely unless massive amounts have been swallowed. Drinking water with >500 mg/L may result in gastrointestinal irritation.
Skin Contact:
No adverse effects expected.
Eye Contact:
No adverse effects expected but dust may cause mechanical irritation.
Chronic Exposure:
No information found.
Aggravation of Pre-existing Conditions:
No information found.

SUMMARY

There is a massive amount of people who are terrified of sharks, and there appears to be no sufficient means of deterring the shark either by electrode, mechanical or chemical which can provide some means of security while being in the water or ocean. The reason for this type of repellent containing this mixture or forms, is to give off a penetrating toxic odor to deter the shark or other large fish from preying on stranded humans or animals, who may or may not be wounded in the water. Even if one were wounded in the water, the strong toxicity and trenchant odor of the repellent may camouflage the smell of blood, therefore deterring the shark or other large fish away from the human or animal.

The toxic smell that would emerge from this method, would substantially escape from harming any human or animal wearing the protective garment containing the shark repellent, as the compound would be submerged in water and exude out in its' periphery. The effects of the shark repellent on human and aquatic life would be unremarkable compared to that of a massive oil spill, but at the same time, be powerful enough to deter a shark (or any other aquatic life) as it can swim away from the repellent as it exudes into the water.

The mixture of these chemical compounds would deter the shark not only by sense of smell, but toxicity to the eyes and gills by which the shark could not tolerate, as these major organs are directly exposed to water. Humans and animals would have the advantage of their heads being above water, whereas the protective garments and devices allow the repellent to drain and penetrate the surface of the water. If necessary, an aquatic mask could be used.

This shark repellent will be effective, as explained in the background of cited articles, because of the proven toxicity, odor, penetrating power, (1. The act or power of penetrating, *Webster's College Dictionary*, to enter or go through the water) chemical composition, and solubility.

BRIEF DESCRIPTION OF DRAWINGS

FIG. 6. Back section of vest.

DETAILED DESCRIPTION

Figure 4:
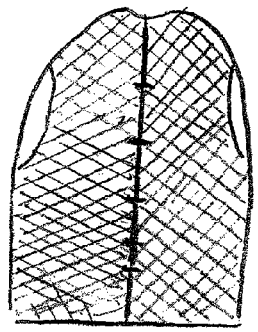
FIG. 4. Front section of vest with mesh
FIG. 5. Cross section of vest with mesh in front and back.
Figure 4:
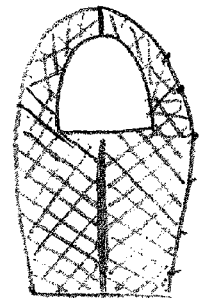
Figure 5:
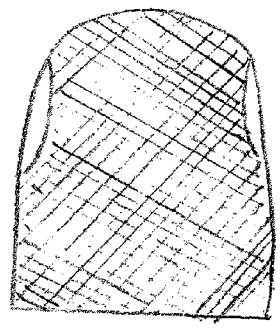

Shark Repellent:

The shark repellent comprises of a mixture of toxic chemical compounds with penetrating power, having a trenchant odor, that is partially soluble when immersed in water.

The shark repellent will be made out of any form, whether it be beads, pellets, gel, liquid gel, liquid, paste, lotion, cream, or the like, and may be soluble or insoluble, and not limited to size or shape. These said forms may be in single form, or in combination, and may consist of the same materials or chemicals as found in crude oil or petroleum, or that of pitch resin, or wood tar, which also may or may not contain turpentine, benzene, bitumen, methanol, charcoal, asphalt, naphthalene, tar, coal, coal tar, asphalt, wood alcohol and may contain other oils, such as crude oil, pine oil, linseed oil, Burmese oil, tea-tree oil, or the like, giving off acidic sting and smell. Included in any of these forms, there may be a coating with a type of polymer. There may also be a type of Bisphenol A, or other type of Polyether ketone included in any single or combination of said forms. Other thickening agents could consist of polysaccharides (optionally together with other thickeners) combined with buffered aqueous or aqueous alcoholic solution containing alkaline earth, metal ions, disintegrating agent, emulsifier, plasticizer and/or surfactants. The beads or pellets, could also be constructed out of plastic or cellophane material, whereas, once popped, would release the odor or chemical containment therein.

*Another version of this repellent would be to simulate the smell in various forms of such toxic materials or substances.

Delivery Systems and Uses of Repellent

These shark repellent delivery systems which include belt, vest, anklets, inner tube or flotation device, and garments are designed with simplicity of use and function. Unlike other complicated designs, these garments have a different design and means of containing shark repellent, which will aid in filling the garment with repellent in an uncomplicated fashion, as well as the repellent itself being soluble.

Keeping mind the prior art of Schneider (U.S. Pat. No. 4,917,280, issued 17 Apr. 1990), this new shark repellent belt will not have individual or single pocket slots containing individual or single pellets inside those slots. Instead, this new belt will be a tubed version, simulating that of an inner-tube, or merely a belt having a hollow enclosure, not limited to shape, to contain a much larger volume of shark repellent pellets or beads.

Description of Belt:

The side of the belt against the wearer could be made of any plastic, resin, polyester or vinyl material, as in any impervious materials used in life vests for nautical purposes. The outside of the belt may have a mesh-like material, constructed or formed out of any material or substance, whether be a woven fabric, metal, plastic, or any means of interlocking, interwoven, or intertwined material, or holes, of open texture, whereas the beads or pellets, or any of the said materials, of said shark repellent, can bleed through the mesh, into the water. The mesh may be attached to the belt by use of stitching, zippering, Velcro, snaps, strings, plastic clips or any other attachment means. The outside of the belt will have, but not be limited to, a flap, opening or pouch made of mesh to insert the pellets or beads, or any form of said shark repellent and may encompass the entire belt in dimension or may have one or more separate flaps. The flaps will be closed by the means of zippering, Velcro, snaps, strings, plastic connections or clips, buttons, or any other attachment/closure devices. The mesh itself may be made of any material or blends of material, whether it be made of metal links, or any woven, knit or knotted fabric of open texture, to allow water to pass through to the pellets or beads.

The belt itself may either have a clip, Velcro, snaps or strings or other attachment or closure device in order to secure it around the waist of the wearer.

Another version of this belt would be to have it completely made out of mesh as described, consisting of a hollow enclosure, not limited to size or shape, whereas the beads or pellets are all exposed to the water through the mesh. The mesh belt will be open on all sides, including the side against the wearer. The mesh belt could be fastened by any attachment device as described.

Aquatic Attach Protection Belt and Chemical Pellets Therefore.

Description of Vest

Here, keeping in mind the prior art invention of Franklin Turner (U.S. Pat. No. 7,351,126, issued 1 Apr. 2008; and U.S. Pat. No. 6,976,894, issued 20 Dec. 2005), the vest will be a combination wet or aquatic vest and may or may not contain a flotation device within. The wet vest or aquatic vest will comprise of a torso portion having a front portion and a rear portion, a pocket or pockets located within the torso portion adjacent to the rear portion. Anywhere on this vest, whether it be front, back, sides, inside or outside, the insertion of the mesh-like material of said material, or holes of open texture, or pocket can be located.

Pockets can also fully encompass the entire front or rear portion of the vest, and are not limited to size.

The mesh-like material can be attached by means of being sewn in, zippered, Velcro, hook and loop, or the like. Within these pockets the mesh-like material will contain the shark repellent that will evaporate into the water.

Description of Inner Tube

The inner tube may be constructed of any material that is either inflatable or floatable, with a containment area located within, on the inner side, or around the tube, whereas shark repellent beads or pellets, or any form of material of said shark repellent as described, may be inserted within that containment area. The tube itself may contain merely holes or openings, or said mesh material, whereas the shark repellent bead, pellets, gel or liquid-gel, or any said form of repellent, can be exposed to water, setting off the pungent odor. The containment area of the tube as described may also made of, or is not limited to, mesh in the way of metal links, resin, film or any woven, knit, or knotted fabric of open texture, to allow water to pass through to the pellets or beads.

Description of Wristbands and Anklets

The shark repellent wristbands and anklets will be made similarly to the shark repellent belt, but smaller in size to fit appropriately around the wrists and ankles. It may be made of any material, and not limited to, metal links, resin or film, or any woven, knit or knotted fabric of open texture, as fore mentioned, to allow water to pass through to the pellets, beads, gel, or liquid-gel, or any of said forms of repellent. The wristband may be attached by means of zipper, Velcro, plastic clips, buttons, snaps, strings. Mesh, or holes of open texture, of wristband or anklet may be on the inner, or outer, side of said band or anklet.

Description of Garment

The garment may be made of any material, that is either impervious or semi-impervious to water, which have pockets or flaps, for containment of shark repellent in said description. The pockets can be made of made of any material, and may, or may not, contain holes of any kind, or a mesh-like material of any kind, not limited to metal links, resin or film, or any woven, knit or knotted fabric of open texture, to allow water to pass through to the pellets, beads, gels or liquid-gel. The pockets or flaps may be attached by means of zipper, Velcro, plastic clips, buttons, snaps, strings. The pockets are not limited to size, and may fully encompass the front or rear portion of the garment, or may be individual pockets. The garment may or may not be full-bodied or full length, with no limitation to length of sleeves or pants, whereas the garment may also be sleeveless.

The garment may also have no limitation on length of pants, whether they be long, short, three-quarter length. The garment may also be closed or fastened by any means of attachment. It may also be slip-on, pull-on, or pull-over.

What is claimed:

1. A shark repelling device comprising a mesh-like material carrier containing crude oil or petroleum in a form selected from the group consisting of beads, pellets, gel, liquid gel, liquid, paste, lotion and cream, wherein the mesh-like material carrier allows water to pass through and an effective shark repelling amount of the crude oil or petroleum bleeds when immersed in water.

2. The shark repelling device according to claim 1, further comprising wood alcohol.

3. The shark repelling device according to claim 1, further comprising benzene.

4. The shark repelling device according to claim 1, further comprising bitumen.

5. The shark repelling device according to claim 1, further comprising pitch resin.

6. The shark repelling device according to claim 1, further comprising turpentine.

7. The shark repelling device according to claim 1, further comprising ethanol.

8. The shark repelling device according to claim 1, further comprising charcoal.

9. The shark repelling device according to claim 1, further comprising coal.

10. The shark repelling device according to claim 1, further comprising coal tar.

11. The shark repelling device according to claim 1, further comprising tar.

12. The shark repelling device according to claim 1, further comprising carbinol.

13. The shark repelling device according to claim 1, further comprising gasoline.

14. The shark repelling device according to claim 1, further comprising kerosene.

15. The shark repelling device according to claim 1, further comprising naphthalene.

16. The shark repelling device according to claim 1, further comprising camphor.

17. The shark repelling device according to claim 1, further comprising tea-tree oil.

18. The shark repelling device according to claim 1, further comprising pine oil.

19. The shark repelling device according to claim 1, further comprising Burmese oil.

20. The shark repelling device according to claim 1, further comprising wood tar.

21. The shark repelling device according to claim 1, further comprising asphalt.

22. The shark repelling device according to claim 1, further comprising naphtha.

23. The shark repelling device according to claim 1, further comprising formaldehyde.

24. The shark repelling device according to claim 1, further comprising sulfur.

25. The shark repelling device according to claim 1, further comprising methanol.

26. The shark repelling device according to claim 1, further comprising chlorine.

27. A method of repelling sharks comprising attaching the shark repelling device according to claim 1 to a human or animal and immersing said device in a body of water which contains sharks.

\* \* \* \* \*

UNITED STATES PATENT AND TRADEMARK OFFICE
CERTIFICATE OF CORRECTION

| | | |
|---|---|---|
| PATENT NO. | : 8,691,253 B1 | |
| APPLICATION NO. | : 12/467455 | |
| DATED | : April 8, 2014 | |
| INVENTOR(S) | : Rhonda Tracy | |

It is certified that error appears in the above-identified patent and that said Letters Patent is hereby corrected as shown below:

In the Drawings

Delete Drawing Sheets 1-5 and substitute therefore with the attached Drawing Sheets 1-5 consisting of formal FIGS. 1-14.

Signed and Sealed this
Third Day of June, 2014

Michelle K. Lee
*Deputy Director of the United States Patent and Trademark Office*

Belt with mesh on inner side.

Cross section of belt with mesh.

Belt with mesh on outer side.

Figure 7:
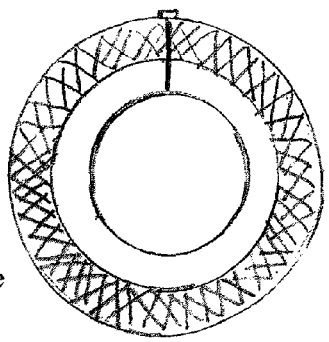
FIG. 7. Wrist band or anklet with mesh on outer side.

Figure 4.
Front section of vest with mesh.
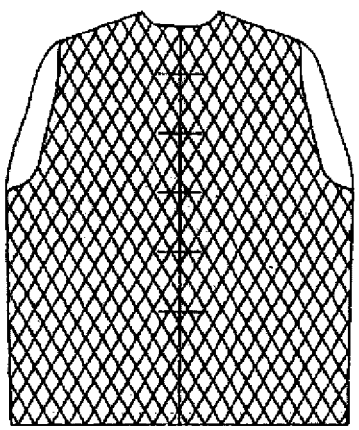
Figure 6.
Back section of vest.
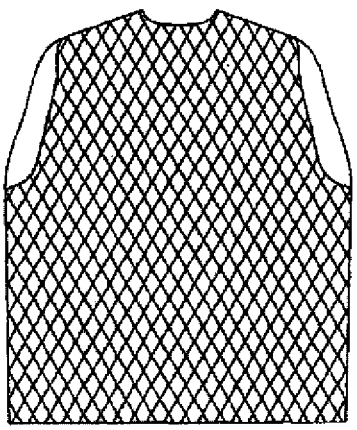
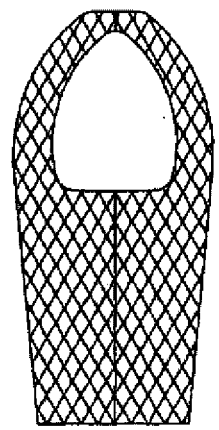
Figure 5.
Cross section of vest with mesh on front and back.
Figure 7.
Wrist band / anklet with mesh on outer side.
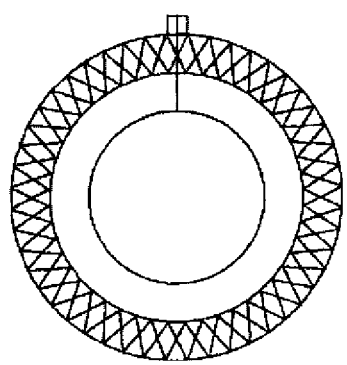

Figure 8:
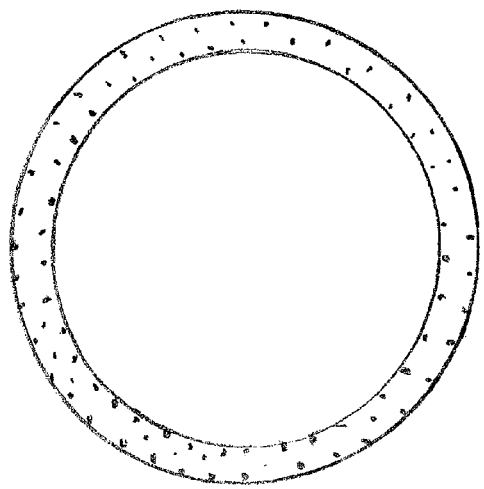
FIG. 8. Inner tube/flotation device with holes.
Figure 9:
FIG. 9. Cross section of inner tube with holes.
Figure 10:
FIG. 10. Cross section of inner tube with mesh
FIG. 11. Inner tube/flotation device with mesh.
Figure 11:
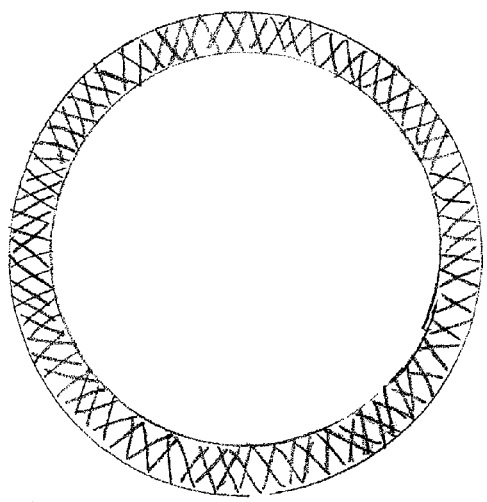
Figure 12:
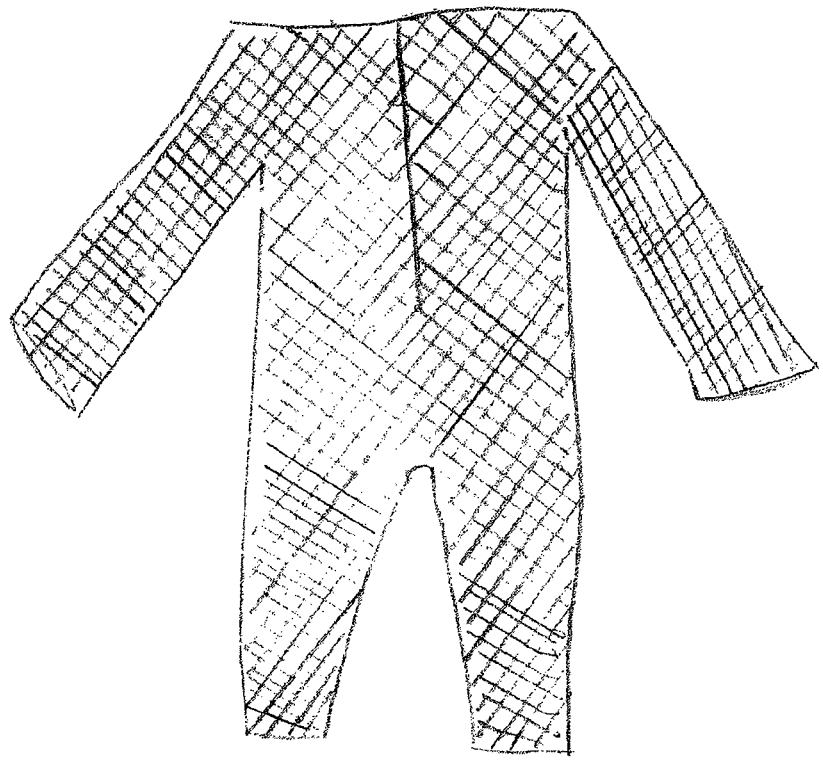
FIG. 12. Front section of garment with mesh.
Figure 13:
FIG. 13. Cross section of garment with semi impervious or impervious layer with mesh.
Figure 14:
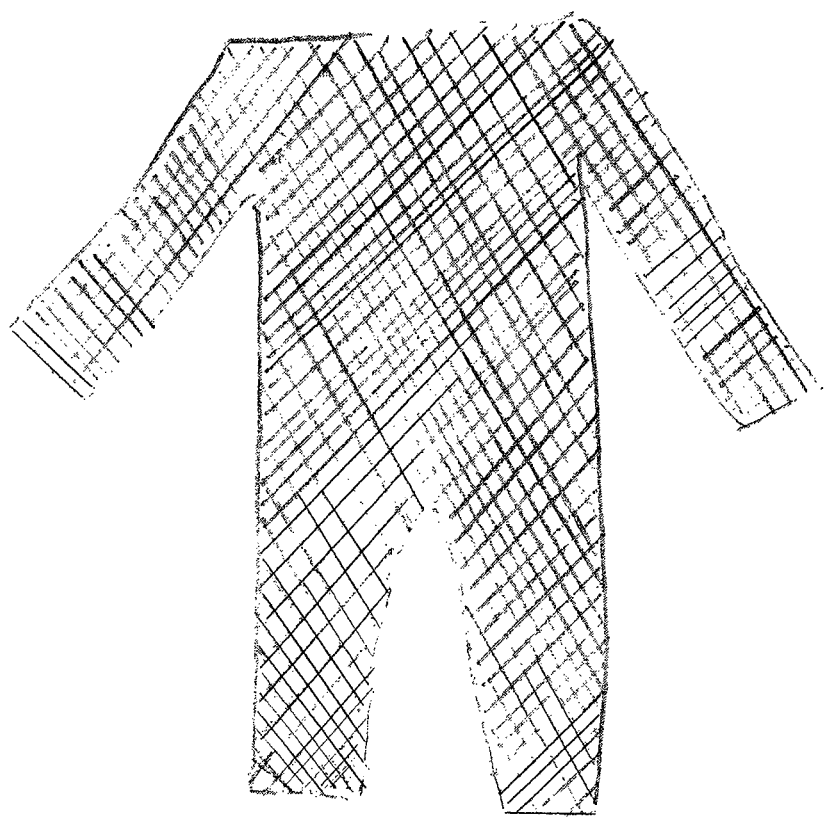
FIG. 14. Back section of garment with mesh.
Figure 1:
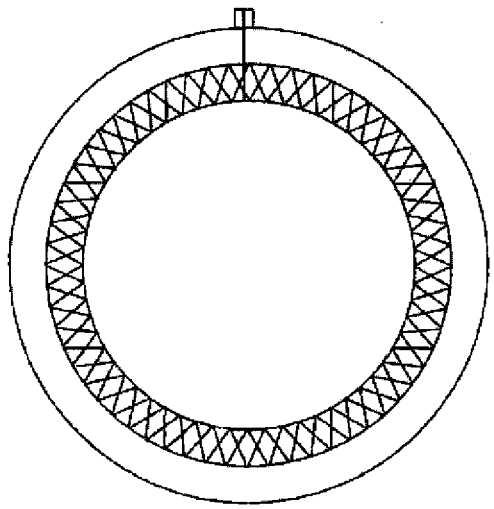
FIG. 1. Belt with mesh on inner side.
Figure 2:
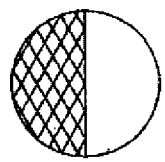
FIG. 2. Cross section of belt and mesh.
Figure 3:
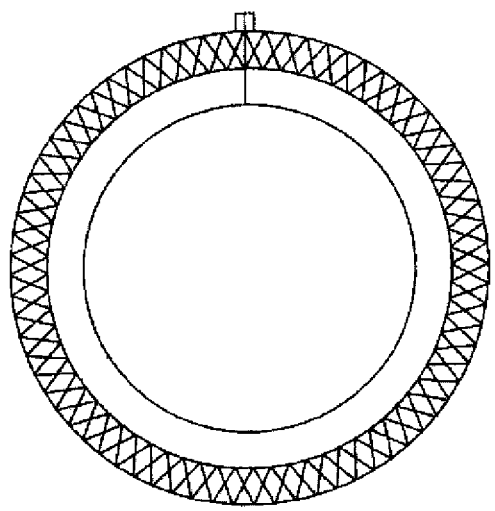
FIG. 3. Belt with mesh on outer side.
Figure 12:
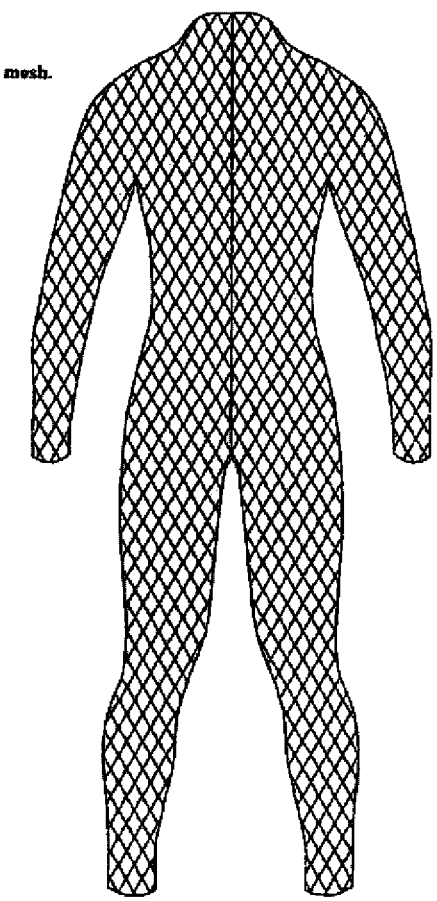
Figure 13:
Figure 14:
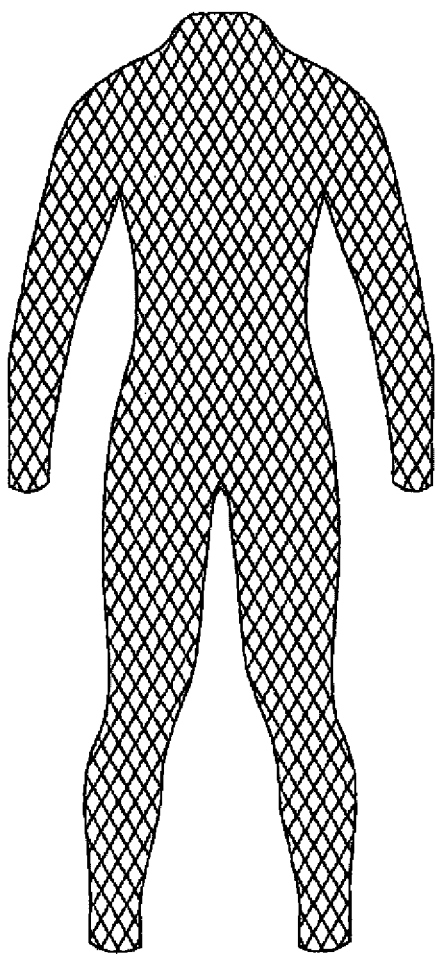

Figure 8.
Inner tube / floatation device with holes.
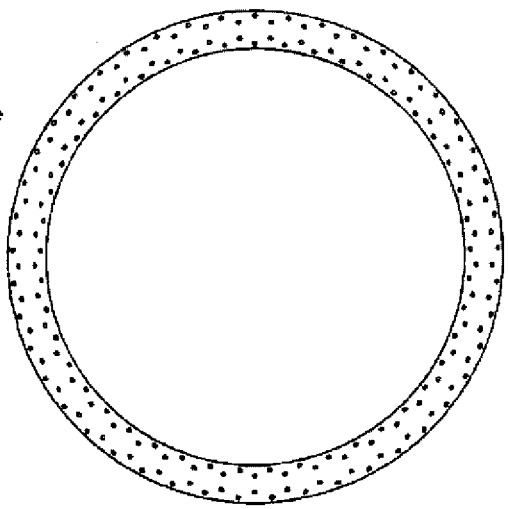
Figure 9.
Cross section of inner tube with holes.
Figure 10.
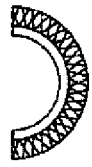
Cross section of inner tube with mesh.
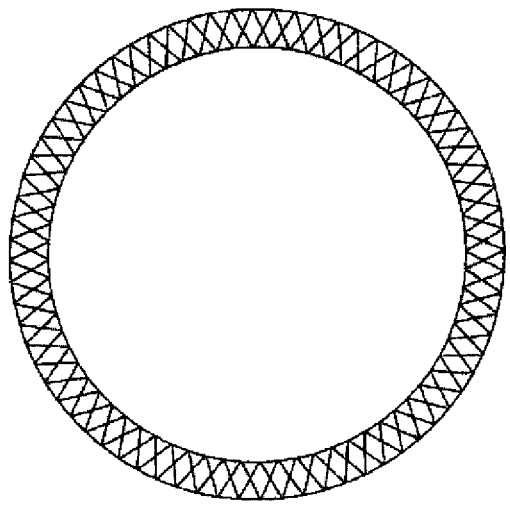
Figure 11.
Inner tube / floatation device with mesh.

Front section of garment with mesh.

Cross section of garment with semi-impervious or impervious layer with mesh.

Back section of garment with mesh.